(12) United States Patent
Rosenstiel

(10) Patent No.: US 6,299,908 B1
(45) Date of Patent: Oct. 9, 2001

(54) COMPOUND AND METHOD FOR MINIMIZING THE APPEARANCE OF CUTANEOUS NEOPLASMS AND DISCOLORATIONS

(76) Inventor: Leonie Rosenstiel, 7542 Bear Canyon Rd., NE., Albuquerque, NM (US) 87109

( * ) Notice: Subject to any disclaimer, the term of this patent is extended or adjusted under 35 U.S.C. 154(b) by 0 days.

(21) Appl. No.: 09/398,335

(22) Filed: Sep. 17, 1999

Related U.S. Application Data

(60) Provisional application No. 60/103,243, filed on Oct. 6, 1998.

(51) Int. Cl.$^7$ .......................... A61K 33/38; A61K 33/06; A61K 31/695; A61K 31/355
(52) U.S. Cl. ......................... 424/618; 424/682; 514/63; 514/458
(58) Field of Search .................................. 424/682, 618; 514/458, 63

(56) References Cited

U.S. PATENT DOCUMENTS 2,103,999 * 12/1937 Muller .
4,016,264 * 4/1977 Clark .
4,349,543 * 9/1982 Jacobi et al. .

OTHER PUBLICATIONS

Derwent English abstract of German Pat. No. 3514724 A, Oct. 1986.*
Derwent English abstract of Austrian Pat. No. 9676379 A, Jul. 1998.*

* cited by examiner

Primary Examiner—Francisco Prats
Assistant Examiner—Susan D. Coe
(74) Attorney, Agent, or Firm—Stephen A. Slusher; Deborah A. Peacock; Joseph Barrera

(57) ABSTRACT

The present invention discloses an organic compound which assists in minimizing the appearance of or removing unwanted skin growths and discolorations without damaging or scarring the skin. The organic compound of the present invention include a mineral from the family of pyrophyllite and organic apple cider vinegar. The ratio of the bentonite to the vinegar is between about 1:1 to 1:1.5, by weight (grams) to by volume (milliliters). The mineral is preferably bentonite or montmorillonite. A method for making and applying the organic compound is also presently disclosed This method includes a first step of providing a mineral from the family of pyrophyllite. In a second step, organic apple cider vinegar is provided. The mineral is then mixed with the vinegar to form a paste. The paste is then applied to areas of the skin upon which there are growths. Preferably, between about 0.18 to about 0.21 grams of the paste should be applied to about every 0.5 cm of the growth.

20 Claims, No Drawings

COMPOUND AND METHOD FOR MINIMIZING THE APPEARANCE OF CUTANEOUS NEOPLASMS AND DISCOLORATIONS

A claim of priority is made to Provisional Application Serial No. 60/103,243 for Substances and Procedures for Removal of Cutaneous Neoplasms with Minimal or No Scars or Damage to Surrounding Tissues with the Filing Date of Oct. 6, 1998.

TECHNICAL FIELD OF THE INVENTION

The present invention is directed to an organic compound. More particularly, the present invention is directed to an organic compound which decreases the appearance of unwanted skin growths and discolorations.

BACKGROUND OF THE INVENTION

Many people experience growths on their skin, such as moles, warts, and the like. To treat such growths, invasive procedures, such as, laser surgery, are typically used. These procedures, while successfully removing the growths, often cause pain and scarring for the patient. More importantly, many patients cannot afford such expensive treatment.

The human body acts in conjunction with vitamins and minerals. Vitamins cannot be assimilated in the body without the aid of minerals. Though the body manufactures a few vitamins on its own, it cannot manufacture any minerals. All tissues and internal fluids of our body contain varying quantities of various minerals. There are minerals contained within the bones, the teeth, soft tissue, muscle, blood, and nerve cells. These minerals are vital to the overall mental and physical well being of any person.

Minerals act as a catalyst for many biological reactions within our bodies, including muscle response, the transmission of messages through the nervous system, the production of hormones, digestion, and the utilization of nutrients in foods. Similarly, minerals can be used to break down many harmful substances which are contained in our bodies. The minerals do this by naturally reacting with vitamins which are contained within these areas.

The need has therefore arisen to provide people with an inexpensive way to enable the body to naturally break down unwanted skin growths while preventing damage to surrounding tissue and permanent scarring.

SUMMARY OF THE INVENTION

The present invention discloses an organic compound which assists in the removal of unwanted skin growths without damaging or scarring the skin. The organic compound of the present invention include a mineral from the family of pyrophyllite and organic apple cider vinegar. The ratio of the bentonite to the vinegar is between about 1:1 to 1:1.5, by weight (grams) to by volume (milliliters). The mineral is preferably bentonite or moritmorillonite A method for making and applying the organic compound is also presently disclosed. This method includes a first step of providing a mineral from the family of pyrophyllite. In a second step, organic apple cider vinegar is provided. The mineral is then mixed with the vinegar to form a paste. The paste is then applied to areas of the skin upon which there are growths. Preferably, between about 0.18 to about 0.21 grams of the paste should be applied to about every 0.5 cm of the growth.

DETAILED DESCRIPTION OF THE INVENTION

While the making using the various embodiments of the present invention are discussed in detail below, it should be appreciated that the present invention provides many applicable inventive concepts which can be embodied in a wider variety of specific contexts. Specific embodiments discussed herein are merely illustrative of the specific ways to make and use the invention and do not limit the scope of the invention. The present invention discloses an organic compound which minimizes the appearance of unwanted skin growths and discolorations without damaging or scarring the skin or tissue. The organic compound comprises a mineral from the family of pyrophyllite and organic apple cider vinegar. The mineral is preferably either Bentonite or Montmorillonite.

Bentonite is a type of clay, which was named by an American Geologist who in about 1890 discovered a clay bed in the vicinity of Fort Benton, Wyoming, and named this clay Bentonite after the location of his find. A main constituent in Bentonite is Mieral Montmorillonite. Bentonite has been recognized as a useful mineral for many applications. The food industry uses Bentonite for refining, decolorizing, purifying, and stabilizing vegetable and animal oils and fats. In the forestry and water conservation industry, Bentonite is used as a powdered fire extinguishing agent. In the chemical industry, Bentonite is used as a catalyst, or catalyst carrier, an insecticide, fungicide, dehydrating agent, and for waste water purification as an absorbent for radioactive materials. In the paper industry, Bentonite is used as a pigment or color developer for carbon-less coping and absorption of impurities in white water systems. Bentonite has also been recognized as applicable in the pharmaceutical industry. This industry mainly uses Bentonite in the area in cosmetics and creams. In the present invention, Bentonite is used because it assists in purifying the skin's, surface and absorbs unwanted impurities.

Montmorillonite clay is highly adsorbent. This clay can quickly neutralize allegiants before they can invade the body and attach themselves to blood cells. Adsorptive surfaces prevent allergic reactions. Montmorillonite clay is often used as an agent in organic formations for respiratory support.

In the present invention the mineral of the family of pyrophyllite is combined with the organic vinegar to form a paste. This paste can be applied to skin growths on the cody. The organic compound of the present invention was successfully produced by the formula presented in EXAMPLE 1, as follows:

EXAMPLE 1

| Organic Constituent | Volume/Weight |
|---|---|
| Pyrophyllite (Bentonite/Montmorillonite) | 15–18 grams |
| Organic Apple Cider Vinegar | 20 milliliters |

The above Organic Compound is preferably produced in a paste form for easily spreading over the affected surface of the skin.

In another embodiment, a process for preparing and applying the organic compound of the present invention is disclosed. In the process of preparation, the cosmetic grade of mineral of the family of pyrophyllite is provided in clay form. Also provided, is organic apple cider vinegar. By mixing the mineral with the vinegar, a paste of the present invention is formed. Once the paste has been formed, it can be applied to skin growths. The proper application of the present invention is to apply the paste for a period of three days to the affected areas. After three days of application, the area should have applied to it Colloidal Silver. The Colloidal Silver is best applied in the amount of 0.1 to 0.2 milliliters per centimeter of growth area. After a day of applying the Colloidal Silver, vitamin E should be applied to the affected area. It is best to apply the vitamin E in the ratio of 0.1 to 0.2 milliliters per centimeter of growth area. Finally, after applying the vitamin E, glycerin, mixed in a 1 to 1 proportion with water (preferably distilled water), should be applied to the affected area, in the ratio of 0.1 to 0.2 milliliters per centimeter of growth area. This step preferably occurs on the third day following the last application of the organic compound. Following the steps mentioned above should assist in minimizing the appearance of, reduce or remove unwanted growths and discolorations from the skin. The entire process may be repeated until the growth shrinks, or is less noticeable.

While this invention has been described in reference to illustrative embodiments, this description is not intended to be construed in a limiting sense. Various modifications and combinations of the illustrative embodiment, as well as other embodiments of the invention, will be apparent to the person skilled in the art upon referenced the description. It is therefore intended that the appended claims encompass any such modifications or embodiments.

What is claimed is:

1. A method for minimizing the appearance of skin growths comprising the steps of:
   (a) providing a paste mixture of a mineral selected from the family of pyrophyllite and at least one vinegar;
   (b) applying said paste to the area of the skin with the growth daily for a period of at least three days;
   (c) applying colloidal silver to the area of the skin with the growth daily for at least one day subsequent to the last day of applying said paste;
   (d) applying vitamin E to the area of the skin with the growth daily for at least one day subsequent to the last day of applying said colloidal silver; and
   (e) applying glycerin to the area of the skin with the growth daily for at least one day subsequent to the last day of applying said vitamin E.

2. The method of claim 1 where in the ratio of s aid mineral to said vinegar is 1:1 to 1:1.5 by weight.

3. The method of claim 1 wherein said mineral comprises approximately about 40 to 50 percent by weight of said paste.

4. The method of claim 1 wherein said vinegar comprises approximately about 50 to 60 percent by weight of said paste.

5. The method of claim 1 wherein said vinegar is raw and unfiltered.

6. The method of claim 1 wherein said mineral is bentonite.

7. The method of claim 1 wherein said mineral is montmorillonite.

8. The method of claim 1 wherein said at least one vinegar comprises cider vinegar.

9. The method of claim 1 wherein said at least one vinegar comprises apple cider vinegar.

10. The method of claim 1 wherein said at least one vinegar comprises organic apple cider vinegar.

11. A method for minimizing the appearance of skin growths comprising the steps of:
    (a) providing a paste mixture of a mineral selected from the family of pyrophyllite and at least one vinegar;
    (b) applying said paste to the area of the skin with the growth daily for a period of at least three days;
    (c) applying vitamin E to the area of the skin with the growth daily for at least one day subsequent to the last day of applying said paste; and
    (d) applying glycerin to the area of the skin with the growth daily for at least one day subsequent to the last day of applying said vitamin E.

12. The method of claim 11 wherein the ratio of said mineral to said vinegar is 1:1 to 1:1.5 by weight.

13. The method of claim 11 wherein said mineral comprises approximately about 40 to 50 percent by weight of said paste.

14. The method of claim 11 wherein said vinegar comprises approximately about 50 to 60 percent by weight of said paste.

15. The method of claim 11 wherein said vinegar is raw and unfiltered.

16. The method of claim 11 wherein said mineral is bentonite.

17. The method of claim 11 wherein said mineral is montmorillonite.

18. The method of claim 11 wherein said at least one vinegar comprises cider vinegar.

19. The method of claim 11 wherein said at least one vinegar comprises apple cider vinegar.

20. The method of claim 11 wherein said at least one vinegar comprises organic apple cider vinegar.

* * * * *